United States Patent [19]

Kuroda

[11] Patent Number: 5,274,431
[45] Date of Patent: Dec. 28, 1993

[54] METHOD AND APPARATUS FOR COUNTING PARTICLES

[75] Inventor: Toshiaki Kuroda, Takasagoshi, Japan

[73] Assignee: Toa Medical Electronics Co., Ltd., Kobe, Japan

[21] Appl. No.: 791,327

[22] Filed: Nov. 14, 1991

[30] Foreign Application Priority Data

Apr. 24, 1991 [JP] Japan .................... 3-122554

[51] Int. Cl.⁵ ................ G01N 15/10; G01N 33/49
[52] U.S. Cl. ........................ 356/36; 356/72; 377/10; 324/71.4
[58] Field of Search ........... 377/10, 11, 12; 356/73, 356/72, 36; 324/71.4

[56] References Cited

U.S. PATENT DOCUMENTS

| | | | |
|---|---|---|---|
| 4,330,745 | 5/1982 | Hayashi | 377/10 |
| 4,522,493 | 6/1985 | Tamagawa et al. | 356/36 |
| 4,586,190 | 4/1986 | Tsuji | 377/10 |
| 4,653,078 | 3/1987 | Aritomi et al. | 377/10 |
| 4,710,021 | 12/1987 | von Behrens | 356/72 |
| 4,747,685 | 5/1988 | Suzuki | 356/36 |
| 5,194,909 | 3/1993 | Tycko | 356/73 |

Primary Examiner—John S. Heyman
Attorney, Agent, or Firm—Jones, Tullar & Cooper

[57] ABSTRACT

The particle counting apparatus is intended to count the number of particles such as blood corpuscles, by passing through a minute aperture, and detecting the particles electrically. In this particle counting apparatus, the liquid specimen is passed into the minute aperture at a specific flow rate by means of a liquid specimen discharge device, and the particles are counted preliminarily, and the dilution proportion of the liquid specimen is determined when the value of this preceding counting is over a specific value. According to this dilution proportion, the liquid specimen discharge device and diluent discharge device discharge so that the flow rates may be as specified, and the mixture is passed through the minute aperture for main counting. In this way, if there are many particles, simultaneous passes do not occur in the detecting region.

2 Claims, 2 Drawing Sheets

METHOD AND APPARATUS FOR COUNTING PARTICLES

BACKGROUND OF THE INVENTION

The present invention relates to method and apparatus for counting particles by passing particles such as blood corpuscles through a minute aperture (minute orifice) and detecting and counting the particles.

An apparatus of this type for counting particles by passing particles such as blood corpuscles through a minute aperture, and detecting the electric charge (for example, the electric resistance) caused when the particles pass through the aperture is known. When measuring blood cells, the inside diameter of the aperture is about 50 to 100 μm, and the length of the aperture is about 60 to 100 μm. This aperture part is the sensitive zone in particle detection. The particle size is several microns.

In a particle counting apparatus of the electric resistance type, since the sensitive zone is broad, simultaneous passes may occur in the sample with many particles, and correction in the number counted is necessary. As the number of particles increases, simultaneous passes increase sharply. In this case, correction in the number counted is possible. But the magnitude of particle signals in simultaneous passes cannot be corrected, and as a result an error occurs in the distribution width of the particles in, and particle distribution or the like. In the electric resistance type, there is a favorable proportional relation between the size of the particle signal and the size of the actual particle. However, in case of a simultaneous pass, plural particle signals overlap to increase the signal size, and a particle signal proportional to the size of the particle is not obtained.

FIG. 3 is a particle size distribution diagram of erythrocytes (red blood corpuscles), in which the ordinate axis denotes the relative frequency. The solid line shows the distribution curve without a simultaneous pass, and the broken line represents the profile with a simultaneous pass. With a simultaneous pass, large particle signal components increase as mentioned above, and the obtained particle size distribution curve (broken line) is distorted.

Also known is an optical type particle counting apparatus for passing a liquid specimen through a minute aperture enclosed with sheath fluid (sheath flow), and detecting light signals from the particles. This is called a flow cytometer. In the optical type, as compared with the electric type, the sensitive zone is narrow, and simultaneous passes hardly occurs so that correction is not necessary. In this case, the sheath flow means a flow covered with a laminar flow liquid (sheath of liquid) around the particle suspension, the particles being arranging neatly in one row at high precision in the middle of the minute aperture to effect passing.

On the other hand, a combined apparatus of the electric type and the optical type is also known. By emitting light to the minute aperture in a direction orthogonal to the flow of particles, signals of scattered light and fluorescence can be detected simultaneously on individual particles. In this case, too, there are problems relating to the size of the particle signals due to simultaneous passes.

The following methods are known to solve the above problems.

(a) To preliminarily dilute the liquid specimen to such an extend that simultaneous passes cannot occur.

(b) To reduce the flow rate of liquid specimen in the sheath flow so as to pass a narrow flow of liquid specimen in the minute aperture.

The method of (a) takes time and labor in diluting the process. Besides, the number of particles is different in each specimen, and the dilution proportion is not known.

The method of (b) takes a long counting time.

OBJECTS AND SUMMARY OF THE INVENTION

It is hence a primary object of the invention to provide a method and apparatus for counting particles without simultaneous passes in the detecting region, even when many particles are contained, the particle counting apparatus having an electric particle detector.

To achieve the above object, the invention provides a method for counting particles for individually detecting particles by passing a liquid specimen suspended with the particles through a minute aperture of a detector in a manner as to enclose the particles with a sheath liquid, and detecting changes due to difference in the electric impedance between the liquid and the particles, or the optical changes of the light emitted to the minute aperture so as to cross the flow of particles, comprising the steps of:

preliminarily counting the number of particles by passing the liquid specimen into the minute aperture at a specific flow rate prior to main counting, determining the dilution proportion of the liquid specimen when the value of the preceding counting is more than a specific value, and main counting comprising passing the liquid specimen and diluent according to the specified dilution proportion, so that the sum of the liquid specimen flow rate Q1 and the diluent flow rate Q2 may be constant to dilute the liquid specimen, and passing the diluted liquid specimen through the minute aperture to count.

Moreover, the invention presents an apparatus for counting particles for individually detecting particles by passing a liquid specimen suspended with the particles through a minute aperture of a detector in a manner as to enclose the particles with a sheath liquid, and detecting changes due to difference in the electric impedance between the liquid and the particles, or the optical changes of the light emitted to the minute aperture so as to cross the flow of particles, wherein liquid specimen discharge means for discharging liquid specimen and diluent discharge means for discharging diluent are disposed parallel to each other.

According to the invention, as an electrical detecting means, the apparatus may also detect not only the electric impedance, as stated above, but also the optical changes by emitting light to the minute aperture so as to cross the flow of the particles. Detection of optical changes is to detect the scattered light or fluorescence emitted from the particles.

The measurement is considered by dividing the preceding measurement by the main measurement. In the preceding measurement, in the first place, the liquid specimen discharge means supplies the liquid specimen at a specific flow rate into the minute aperture, and particles are counted, and an approximate number of particles in this liquid specimen is determined. On the basis of this approximate value, it is judged whether simultaneous passes may occur or not, and the degree of dilution to avoid simultaneous passes is assessed.

According to the invention, the diluent discharge means is also provided, and on the basis of the result of the preceding measurement, in the main measurement, the liquid specimen discharge means and the diluent discharge means are operated so as to achieve the specified flow rates, respectively. If there are many particles, the diluted liquid specimen is measured in the main count, simultaneous passing does not occur. Meanwhile, since the sum of the flow rates of the liquid specimen and the diluent is constant, and the flow rate balance of the sheath liquid and the diluted liquid specimen is constant, the diameter of the liquid specimen flow at the minute aperture is also constant.

DETAILED DESCRIPTION OF THE PREFERRED EMBODIMENTS

Figure 1:
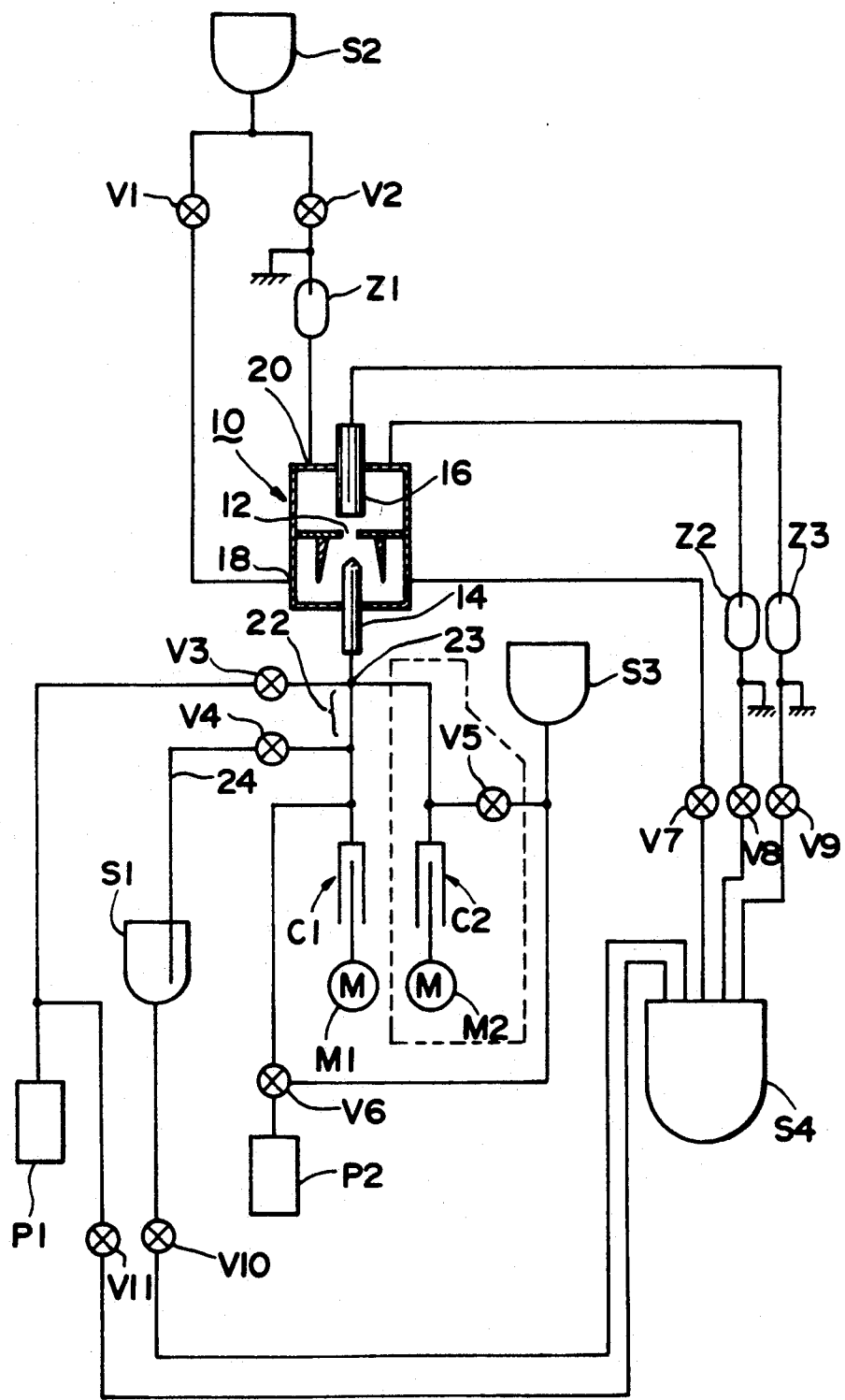
FIG. 1 is a fluid circuit diagram showing an embodiment of a particle counting apparatus of the invention.

Referring now to the drawings, some of the preferred embodiments of the invention are described in detail below.

FIG. 1 is a fluid circuit diagram showing an embodiment of a particle counting apparatus of the invention. The portion enclosed by the broken line is the block added in the invention. Numeral 10 is a particle detector. At the upstream side (the lower side in the drawing) of liquid across a minute aperture 12, a nozzle 14 for discharging a liquid specimen from one end is disposed, and at the downstream side (the upper side in the drawing), a recovery pipe 16 for collecting the measured liquid is provided.

At the other end of the nozzle 14, liquid specimen discharge means C1 for supplying the liquid specimen at a specific flow rate (for example, a syringe type driven by stepping motor M1) is disposed.

When valves V3, V4 are open and pump P1 is in the suction mode, the liquid specimen (blood specimen diluted to specific proportion) in a liquid specimen chamber S1 is sucked by a specified amount to fill up a charging line 22 near the nozzle.

Figure 2:
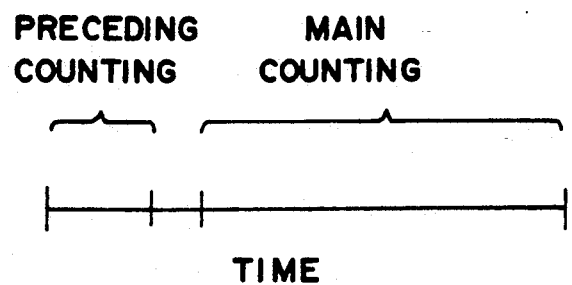
FIG. 2 is a sequence diagram of particle counting in the invention.
Figure 3:
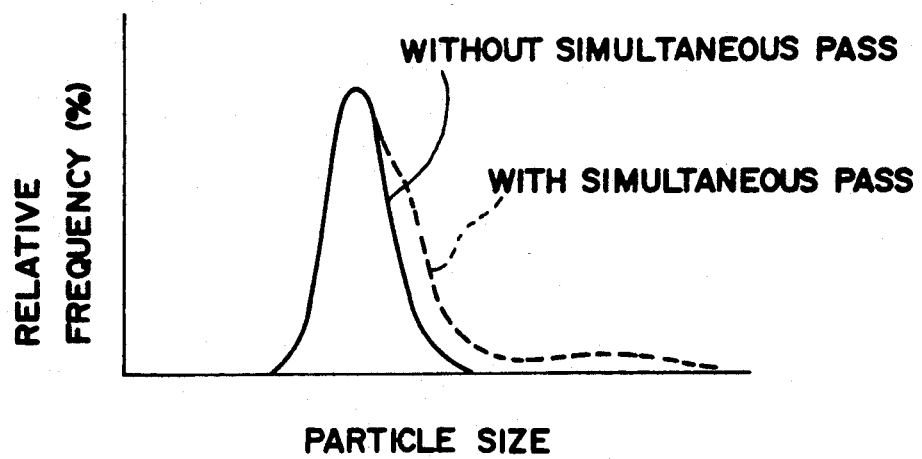
FIG. 3 is a particle size distribution diagram of erythrocytes.

FIG. 2 is a sequence diagram for counting in the invention. First, a preceding counting is done for a short time (for example, 1 second). The valves V3, V4 are closed, valves V1, V2, V9 are open, and the liquid specimen discharge means C1 pushes the liquid specimen at a specific flow rate, and as a result the liquid specimen in the charging line 22 is discharged from the nozzle 14 toward the minute aperture 12. On the other hand, a positive pressure (a pressure higher than the atmospheric pressure) is applied to a sheath liquid chamber S2, and the sheath liquid is also discharged into the detector 10 from a feed port 18, thereby forming a sheath flow, and the particles in the liquid specimen flow are located neatly in the middle of the minute aperture 12. The particles passing through the minute aperture 12 are covered with a back sheath liquid discharged from a feed port 20, recovered in the recovery pipe 16, and discharged into a waste liquid chamber S4.

During the preceding counting, the number of particles in this specimen is approximately calculated. If the number of particles is many, simultaneous passes may occur. Therefore, in the case of a large number of particles, the liquid specimen to be presented for counting is slightly diluted. The relation between the number of particles and the possibility of simultaneous passes is known. Accordingly, by preceding counting, it is known whether dilution of specimen is necessary or not, and the required degree of dilution is also known.

Next is the main counting. In this apparatus, not only the liquid specimen discharge means C1, but also the diluent discharge means C2 (for example, of the same type as the liquid specimen discharge means) for supplying the diluent at a specific flow rate is connected to the other end of the nozzle 14. The connecting position is the end of the charging line 22 closer to the nozzle 14. The diluent discharge means C2 and the diluent chamber C3 are connected through a valve V5. Supposing the discharge flow rates of the liquid specimen discharge means C1 and diluent discharge means C2 to be respectively Q1, Q2, the particle concentration would then be Q1/(Q1+Q2) times, and the two are mixed in the passage from the charging line end 23 to the front end of the nozzle 14, and discharged from the tip of the nozzle 14. By varying the ratio of Q1, Q2, it is possible to change only the dilution proportion, while the sum (Q1+Q2) of the liquids discharged from the nozzle 14 does not vary.

Meanwhile, although it is possible to reduce the simultaneous passes by varying the discharge flow rate of the liquid specimen discharge means C1 only without installing diluent discharge means C2, the balance of the sheath liquid and the liquid specimen is changed, and the thickness of the liquid specimen flow in the minute aperture 12 is changed. When the thickness of the liquid specimen flow varies, the manner of the simultaneous passes of particles varies, too. For example, by counting the liquid sample discharge flow rate at ½ and multiplying the result by 2, the correct number of particles is not obtained.

By diluting the liquid specimen, it is designed, according to the invention, not to change the flow rate of the specimen.

After the measurement, the valve V10 is open, and a liquid specimen left in the liquid specimen chamber S1 is discharged. Then the valve V4 is open, and the valve V6 opens, and the pump P2 is placed in the discharge mode, so that the liquid specimen suction line 24 and the liquid specimen chamber S1 are cleaned. As the cleaning solution, the diluent may be used. The charging line 22 is cleaned when the valves V4, V3 are open and the pump P1 is set in the suction mode. Meanwhile, the liquid sucked by the pump P1 is discharged into the waste liquid chamber S4 as the valve V3 is closed, the valve V11 is opened, and the pump P1 is set in the discharge mode.

By opening the valves V1, V7, V2, V8 and applying a positive pressure to the sheath liquid chamber S2, the inside of the detector 10 can be cleaned. Incidentally, Z1, Z2, Z3 are insulation chambers for electrically insulating the flow passage.

Thus, in this embodiment, the specimen (liquid specimen) with many particles is diluted, while the specimen with a few particles is not, so that any specimen may be counted in a range free from simultaneous passes. If diluted uniformly, there is no problem with the specimen having many particles, but in the specimen with a few particles, the number of particles detected is small, and the counting precision is lowered.

As thus arranged, the invention brings about the following benefits.

(1) The particle counting method of the invention comprises a preceding counting step, a step of determining the dilution proportion, and a main counting step of, in which preceding counting is done before the main counting to determine the dilution proportion in the case of a specimen having a large counting associated therewith, so as to induce simultaneous passes. The liquid specimen is diluted by this dilution proportion to perform the main counting, so that the particles may be counted precisely without causing simultaneous passes. Besides, the sum of the liquid specimen flow rate and the diluent flow rate is always constant, and the flow rate balance of the sheath liquid and the diluted liquid specimen is constant, and also the diameter of the liquid specimen flow at the minute aperture is constant, so that accurate counting is possible.

(2) The particle counting apparatus of the invention comprises diluent discharge means, and it discharges the diluent simultaneously with the liquid specimen discharge in the case of a specimen with many particles so as to cause simultaneous passes. The mixture of the two, that is, the diluted liquid specimen is supplied into the minute aperture of the detector. Therefore, in this case, simultaneous passes do not occur, and particle counting precision is enhanced.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method for counting particles by passing a liquid specimen having the particles suspended therein through a minute aperture of a detector, the liquid specimen being enclosed with a sheath liquid, and the particles being counted by detecting changes due to difference in the electric impedance between the liquid and the particles, or by optical changes of the light irradiated to the minute aperture so as to cross the flow of particles, the method comprising the steps of:

preliminarily counting the number of particles by passing the liquid specimen into the minute aperture at a specific flow rate determined by the particles in the liquid specimen combined with the sheath liquid, determining the dilution proportion of the liquid specimen when the value of the preliminary counting is more than a specific value, and main counting by passing the liquid specimen and a diluent liquid according to a specified dilution proportion, so that the sum of the liquid specimen flow rate and the diluent liquid flow rate may be constant to dilute the liquid specimen, and pass the diluted liquid specimen through the minute aperture to count.

2. An apparatus for counting particles by passing a liquid specimen having the particles suspended therein through a minute aperture of a detector, the liquid specimen being enclosed with a sheath liquid, and the particles being counted by detecting changes due to difference in the electric impedance between the liquid and the particles, or by optical changes of the light irradiated to the minute aperture so as to cross the flow of particles, comprising:

a particle detector having a minute aperture;

a nozzle situated adjacent to said minute aperture for discharging a liquid specimen to said particle detector;

a charging line connected to said nozzle;

liquid specimen discharge means connected to said charging line for discharging liquid specimen to said nozzle through said charging line; and diluent liquid discharge means for discharging diluent liquid in a direction which is parallel to the liquid specimen discharged from said charging line.

* * * * *

UNITED STATES PATENT AND TRADEMARK OFFICE
CERTIFICATE OF CORRECTION

PATENT NO. : 5,274,431

DATED : December 28, 1993

INVENTOR(S) : Toshiaki Kuroda

It is certified that error appears in the above-identified patent and that said Letters Patent is hereby corrected as shown below:

Claim 2, column 6, line 29, "comprising:" should be moved to line 28, after "particles,".

Signed and Sealed this

Twelfth Day of July, 1994

Attest:

BRUCE LEHMAN

*Attesting Officer*     *Commissioner of Patents and Trademarks*